United States Patent [19]

Kurucz

[11] Patent Number: 4,844,074

[45] Date of Patent: Jul. 4, 1989

[54] METHOD AND APPARATUS FOR INTRODUCING A FLUID INTO A HUMAN OR ANIMAL ORGANISM AS WELL AS METHOD AND HEATING DEVICE FOR TEMPERATURE CONTROL

[75] Inventor: József Kurucz, Budapest, Hungary

[73] Assignee: Rolitron Muszaki-Fejleszto Kisszovetkezet, Budapest, Hungary

[21] Appl. No.: 165,279

[22] PCT Filed: Apr. 10, 1987

[86] PCT No.: PCT/HU87/00018

§ 371 Date: Feb. 1, 1988

§ 102(e) Date: Feb. 1, 1988

[87] PCT Pub. No.: WO87/06140

PCT Pub. Date: Oct. 22, 1987

[30] Foreign Application Priority Data

Apr. 11, 1986 [HU] Hungary ................................. 1536

[51] Int. Cl.⁴ ............................................. A61F 7/12
[52] U.S. Cl. .................................. 128/401; 604/114; 219/330; 236/91 F
[58] Field of Search ........................ 128/401; 604/114; 219/330, 313; 236/91 F, 20 R

[56] References Cited

U.S. PATENT DOCUMENTS

| | | | |
|---|---|---|---|
| 2,087,586 | 7/1937 | Tishman | 604/114 X |
| 3,174,298 | 3/1965 | Kleiss | 236/91 F |
| 4,167,663 | 9/1979 | Gipanzow, Jr. et al. | 604/114 X |
| 4,286,377 | 9/1981 | Hurko et al. | 29/612 |
| 4,309,592 | 1/1982 | Boeuf | 219/291 |
| 4,314,143 | 2/1982 | Bilstad et al. | 219/497 |
| 4,464,563 | 8/1984 | Jewett | 219/330 X |

FOREIGN PATENT DOCUMENTS

| | | |
|---|---|---|
| 0112104 | 6/1984 | European Pat. Off. . |
| 0175528 | 3/1986 | European Pat. Off. . |
| 0138171 | 7/1986 | European Pat. Off. . |
| 1914529 | 12/1970 | Fed. Rep. of Germany . |
| WO84/042 | 10/1984 | PCT Int'l Appl. . |

Primary Examiner—William E. Wayner
Attorney, Agent, or Firm—Limbach, Limbach & Sutton

[57] ABSTRACT

Process and device for introducing a physiological fluid at a prescribed temperature in human and animal organisms. The fluid is pumped through a regulated heating means (59) into a gravity-feed container (95), then led by natural gravity out of the gravity-feed container (95) through the same heating means (59) into the organism. While the fluid is being pumped into the gravity-feed container (95, the temperature of the fluid entering the heating means (59) is measured and on the basis of the temperature measured the heating means (59) is set to a temperature or a corresponding heat flow which produces essentially the prescribed temperature of the fluid leaving the heating means (59). While the fluid is being led by natural gravity, the temperature of the heating means (59) is regulated until the prescribed temperature of the fluid is obtained. A heating means (59) suitable for this device comprises at least two heating lateral walls (28, 128) and a channel (47) passing between them. Each side wall (28, 128) has a heating resistance net and a temperature sensor. The resistance network is composed of a heating foil pattern (2, 102) formed on the side of an electrically isolating base plate (1, 101) facing the medium to be heated. On the other side of the base plate (1, 101) is formed a sensor foil pattern (3, 101) forming a temperature sensing resistance and covered with an isolating layer (15, 115).

18 Claims, 9 Drawing Sheets

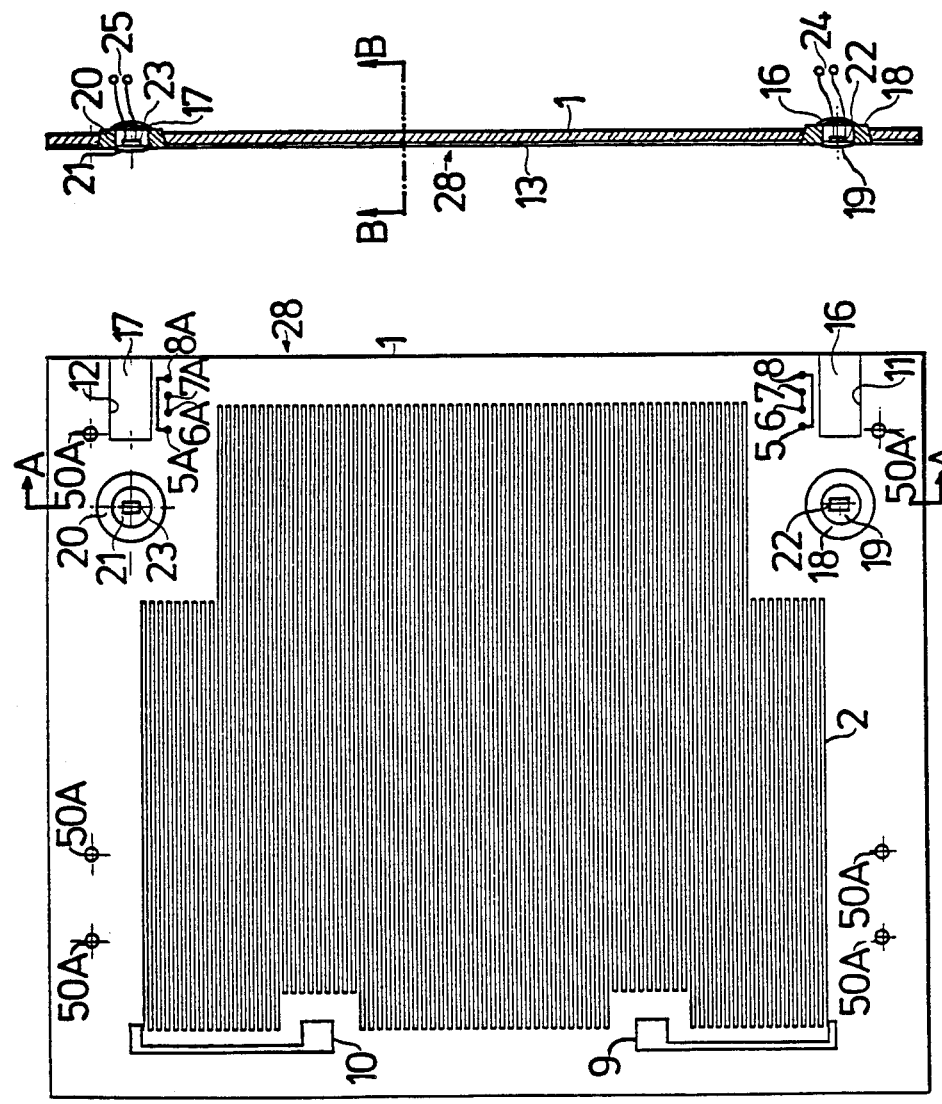

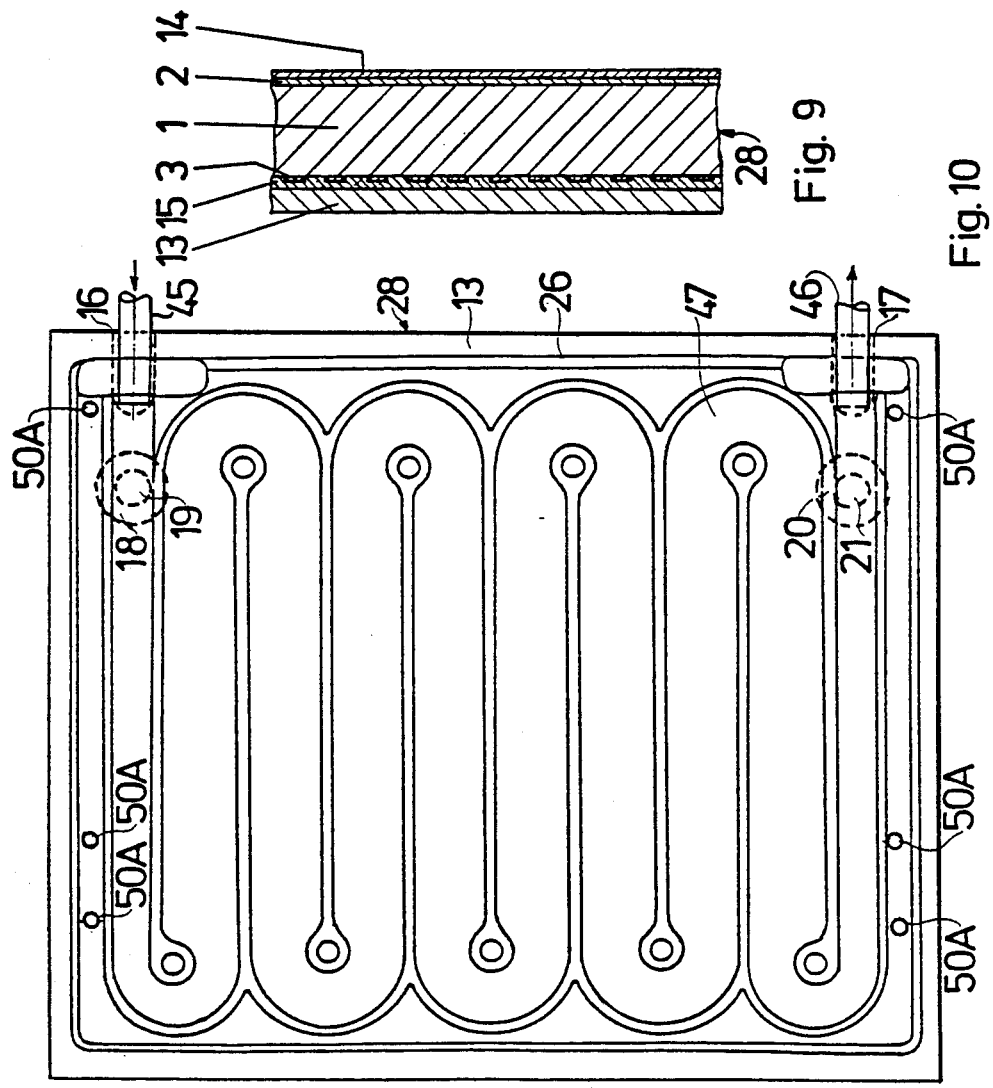

METHOD AND APPARATUS FOR INTRODUCING A FLUID INTO A HUMAN OR ANIMAL ORGANISM AS WELL AS METHOD AND HEATING DEVICE FOR TEMPERATURE CONTROL

TECHNICAL FIELD

The invention relates to a method and an apparatus for introducing a physiological fluid into a human or animal organism as well as an appropriate method and heating device for the control of the temperature of a flowing medium.

BACKGROUND ART

For the control of the temperature of flowing media a solution is known according to which the temperature of the medium discharging from a heating device is measured and the heating of the heating device is controlled by a feedback control circuit so that the medium discharging from the heating device is of a prescribed temperature. With this solution, the control circuit follows relatively slowly the changes in the flow rate or in the temperature of the medium entering the heating device. Consequently, this control is not quick enough especially if the temperature of a smaller quantity of medium has to be controlled.

In another known solution, the flowing medium is led through a heating device of high heat capacity, set to the prescribed temperature. This solution is used e. g. in case of introducing a physiological fluid into a human organism where the safety requirements do not permit that the heating device is of a higher temperature than the prescribed temperature of the fluid. In a known method, the physiological fluid to be introduced is conducted through a spiral hose arranged in a thermostatic water bath.

EP-A-No. 112-104 relates to an apparatus for peritoneal dialysis where the dialysing fluid is pumped through a flat bag arranged between two heating plates of high-heat capacity into a gravity tank and conducted therefrom through the same bag by gravity into the peritoneal cavity of the patient. The heating plates are maintained continuously at body temperature. This temperature control is based also on the fact that the medium flowing slowly enough through a heating device of high heat capacity will achieve the prescribed temperature at the outlet. This control method can be applied only in the case of small flow rates, it does not take into consideration the changes of temperature of the entering fluid, requires a relatively voluminous heating device of high energy consumption and is less applicable due to its time-lag for a follow-up control of the temperature.

DISCLOSURE OF INVENTION

The purpose of the present invention is to provide a method and an apparatus which render it possible to reduce the time of treatment when introducing a physiological fluid. For this purpose a method for controlling the temperature and a heating device are also developed by means of which the temperature of a flowing medium can be controlled with lower energy consumption, quickly and with high accuracy.

Accordingly, the invention relates on the one hand to a method for introducing a physiological fluid into a human or animal organism at a prescribed temperature, wherein the fluid is pumped through a controlled heating device into a gravity tank and then introduced from the gravity tank through the same heating device into the organism by gravity. According to the invention, during the pumping into the gravity tank the temperature of the fluid entering the heating device is measured and, on the basis thereof, a temperature or a heat flux causing substantially the prescribed temperature of the fluid discharging from the heating device is set in the heating device, and during the introduction by gravity the temperature of the heating device is controlled to the prescribed temperature of the fluid.

According to the invention, there are two different temperature controls, namely that at the pumping into the gravity tank and that at the introduction into the organism. In the latter case, taking into consideration the safety requirements, the temperature of the heating device is set at least approximately to the prescribed temperature of the fluid. However, during the pumping into the gravity tank, a quicker, controlled heating of the entering fluid occurs by means of the heating device. This may be achieved so that the temperature of the entering fluid is measured and on the basis thereof—being aware of the parameters of the heating device, the flow rate and the specific heat of the fluid—the temperature or the heat flux is set in the heating device so that the temperature of the fluid discharging from the heating device is at least approximately as high as the prescribed value. When pumping, it is sufficient that the temperature of the fluid entering the gravity tank corresponds only approximately to the prescribed temperature since during the introduction into the organism the fluid flows once more through the heating device set to the prescribed temperature.

Further on, the subject matter of the invention is an apparatus for introducing a physiological fluid in a human or animal organism at a prescribed temperature, which comprises a pump for delivering the physiological fluid through a heating device provided with a control system into a gravity tank and a duct for introducing the fluid from the gravity tank through the same heating device into the organism. According to the invention, the control system of the heating device comprises a control circuit for setting the temperature or the heat flux in the heating device and for this control circuit a reference unit producing a varying reference value altering proportionally to a measured temperature of the fluid entering the heating device during the delivery into the gravity tank and a constant reference value for maintaining the heating device at the prescribed temperature of the fluid during the introduction into the organism, and an input of this reference unit is connected to an output of a first transducer measuring the temperature of the fluid entering the heating device.

In an embodiment of the apparatus, the reference unit has also another input connected to an output of a second transducer measuring the temperature of the fluid discharging from the heating device, and means for superimposing a signal corresponding to the difference between the prescribed temperature of the fluid and the measured temperature of the discharging fluid onto the varying reference value.

On the other hand, the invention relates to a method for controlling the temperature of a flowing medium, wherein the temperature of the flowing medium is measured and a heating device for heating the flowing medium is correspondingly controlled so that the medium discharging from the heating device is always of a prescribed temperature. According to the invention, the temperature of the medium entering the heating device is measured and—on the basis of the measured temperature, as well as the specific head, the flow rate and the prescribed temperature of the discharging medium—a temperature or a heat flux causing substantially the prescribed temperature of the discharging medium is set in the heating device, and at the same time the temperature of the discharging medium is also measured and the temperature or heat flux set in the heating device is varied according to the difference between the prescribed temperature and the measured temperature of the discharging medium.

In the case of this method, the temperature of the medium entering the heating device is continuously measured and in the heating device a temperature or a heat flux is set which ensures the prescribed discharge temperature at the measured entering temperature. Obviously, this is valid only for a medium of given specific heat and flow rate. If the flow rate can considerably vary, the flow rate shall also be measured before the measurement of the temperature of the entering medium, and the setting shall be made by taking this fact into consideration. If, however, the flowing medium is circulated by means of a pump of constant delivery capacity, the flow rate can be regarded as constant with a good approximation. In accordance with the invention, this open loop setting of the heating device/without feedback/ is varied according to the difference between the prescribed temperature and the measured temperature of the discharging medium. This continuous variation is made in a closed loop /with feedback/ and ensures the prescribed temperature of the discharging medium with a high accuracy. The solution is suitable both for a value maintaining temperature control and for a follow-up temperature control. In the case of a relatively stable flow rate, the variation of the temperature or heat flux setting in the heating device is advantageously restricted to ±30%, preferably to ±10% in order to avoid excessive oscillations in the control system at the staring or in the case of sudden changes in the temperature of the entering medium. The method according to the invention renders it possible to provide a quick and simultaneously high accuracy temperature control.

In an embodiment, the setting of the temperature or heat flux in the heating device occurs so that the heating of the heating device is controlled on the basis of the temperature or heat flux measured in the heating device by means of a reference value corresponding to the temperatures of the entering and discharging medium.

The invention further provides a heating device suitable for the above method and for the above apparatus, comprising at least two heating side walls and channel for the medium to be heated therebetween, wherein each side wall is provide with at least one heating resistance network made of a conductive material and at least one temperature sensor for measuring the temperature of the side wall. According, to the invention, the heating resistance network is made of a heating foil pattern formed on a side of an electrically insulating supporting plate, which side is opposite to the medium to be heated, and on a side of the supporting plate, which side is towards the medium to be heated, a sensing foil pattern made of a conductive material and constituting a temperature sensing resistance is formed, and this sensing foil pattern is covered with an insulating layer. It is especially advantageous, if the medium to be heated is inhomogeneous or of a poor thermal conductivity, that on the insulating layer a temperature equalizing layer made of a material of good thermal conductivity, e. g. a copper or aluminum plate thinner than 2 mm is arranged.

The heating device according to the invention makes a very quick and high accuracy temperature control of flowing media possible due to the low time-lag of the heating device and to the good measurability of its temperature. The medium to be heated may be liquid or gaseous.

The invention will now be described by means of the embodiments illustrated in the accompanying drawings.

BRIEF DESCRIPTION OF DRAWINGS

FIG. 7 is a view of the other side of the supporting plate provided with a heating foil pattern, FIG. 8 is a sectional view taken along line A—A of FIG. 7, FIG. 9 is a partial sectional view taken along line B—B of FIG. 8, FIG. 10 is a view of the side according to FIG. 7 of the side wall provided with a bag constituting a channel for the fluid between the side walls.

MODES FOR CARRYING OUT THE INVENTION

Figure 5:
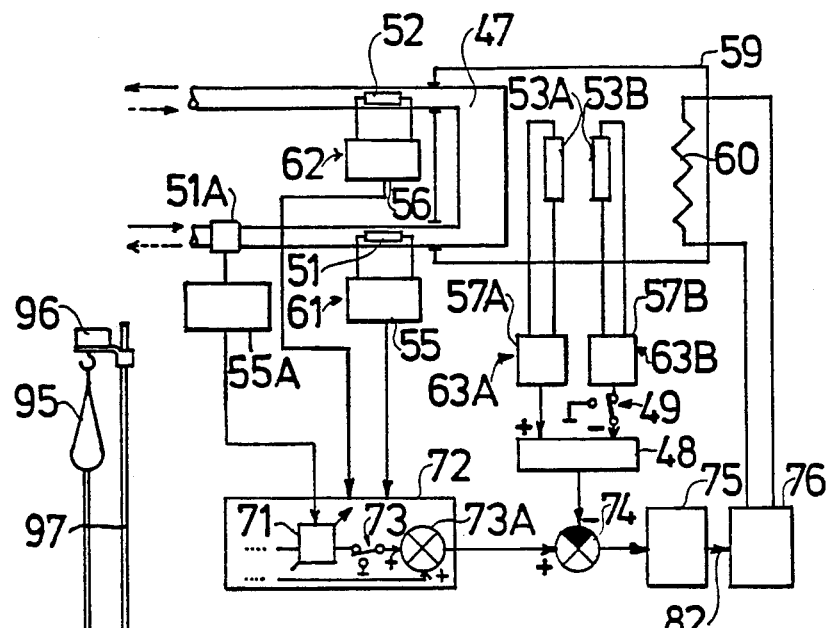
FIG. 5 is a block diagram of a further embodiment of the temperature control system of the apparatus according to FIG. 1.

In the drawings identical elements and elements of identical functions, respectively, are indicated by the same reference signs.

Figure 1:
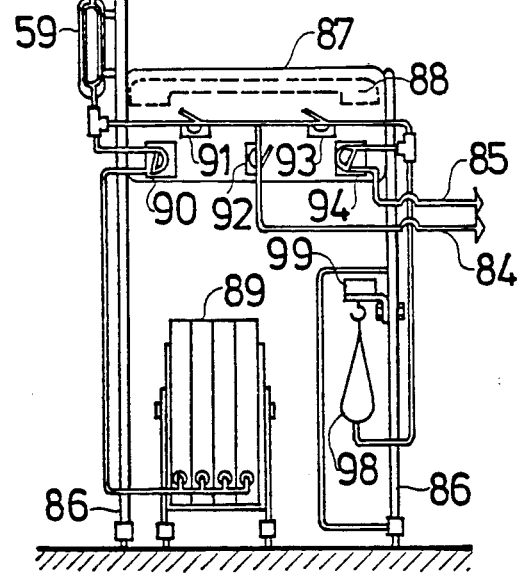
FIG. 1 is a schematic drawing of an apparatus for introducing a physiological fluid into a human organism, according to the invention.

In FIG. 1 an apparatus for peritoneal dialysis demonstrating the use of the apparatus according to the invention is shown, which comprises a heating device 59 according to the invention. The apparatus has a control unit 87 attached to a supporting frame 86 and the control unit 87 is provided with an operating and indicating unit 88. To the supporting frame 86 a supporting bar 97 is also attached upon which a gravity tank 95 is suspended by the intermediation of a dynamometer 96. The apparatus delivers the dialysing solution from a tank 89 through a duct by means of a roller pump 90 via a heating device 59 fastened to the supporting frame 86 into a gravity tank 95. The roller pump 90 is a device known by itself which can deliver the fluid under sterile conditions. During the filling process the valve 91 is closed and the control unit 87 controls the heating device 59 so that the fluid entering the gravity tank 95 is substantially of a temperature prescribed for the introducing into the peritoneal cavity of the patient. As soon as the fluid in the cavity tank 95 reaches the prescribed quantity, the control unit 87 stops the roller pump 90 on the basis of a signal of the dynamometer 96 and thus, the filling is finished.

Now, it comes the introduction of the dialysing fluid being in the gravity tank 95 into the peritoneal cavity of the patient by the force of gravity. For this purpose, the control unit 87 opens the valves 91 and 92 towards a duct 84 conducting to the patient and keeps the valve 93 closed. The roller pump 90 being out of operation provides also for a blocking. During the introduction, the control unit 87 controls the heating device 59 in such a manner that it is always at the temperature prescribed for the introduction. Consequently, the fluid somewhat cooled down due to a possible waiting in the gravity tank 95 discharges from the heating device 59 always at the prescribed temperature irrespective of the flow rate. The flow rate can be dependent on numerous factors such as the state of the catheter introduced into the patient, the condition of the patient, etc. When the required fluid quantity is discharged from the gravity tank 95 as indicated by the dynamometer 96, the control unit 87 closes the valves 91 and 92 and the introduction process is finished.

If the dialysing solution dwelled for an appropriate period in the peritoneal cavity of the patient, it has to be discharged similarly by the gravity. For this purpose, the control unit 87 opens the valves 92 and 93, keeps the valve 91 closed and does not operate the roller pump 94. In this way, the dialysing solution flows into a lower collecting tank 98 arranged on the supporting rame 86 by the intermediation of a dynamometer 99. The dynamometer 99 serves for the measurement of the quantity of the dialysing solution discharged from the patient. At the end of the discharging process the control unit 87 closes the valves 92 and 93.

Now, the fluid collected in the collecting tank 98 has to be drained into the sewage system though a duct 85. For this purpose, the control unit 87 lets the roller pump 94 operate and at the same time keeps the valve 93 closed. At the end of the draining the control unit 87 stops the roller pump 94.

If the control unit 87 registers any irregularity in the course of the introduction process, e. g. the temperature of the fluid flowing out of the heating device 59 is too hight, it interrupts the introduction and drains the fluid into the collecting tank 98. For this purpose, the control unit 87 closes the valve 92 and opens the valve 93.

The above described processes can take place not only in succession but in some cases also simultaneously. Accordingly, the discharge of the dialysing fluid from the patient may take place simultaneously with the filling of the gravity tank 95. Simultaneously with the introduction of the dialysing solution into the patient, the previously discharged dialysing fluid can be drained into the sewage system.

Figure 2:
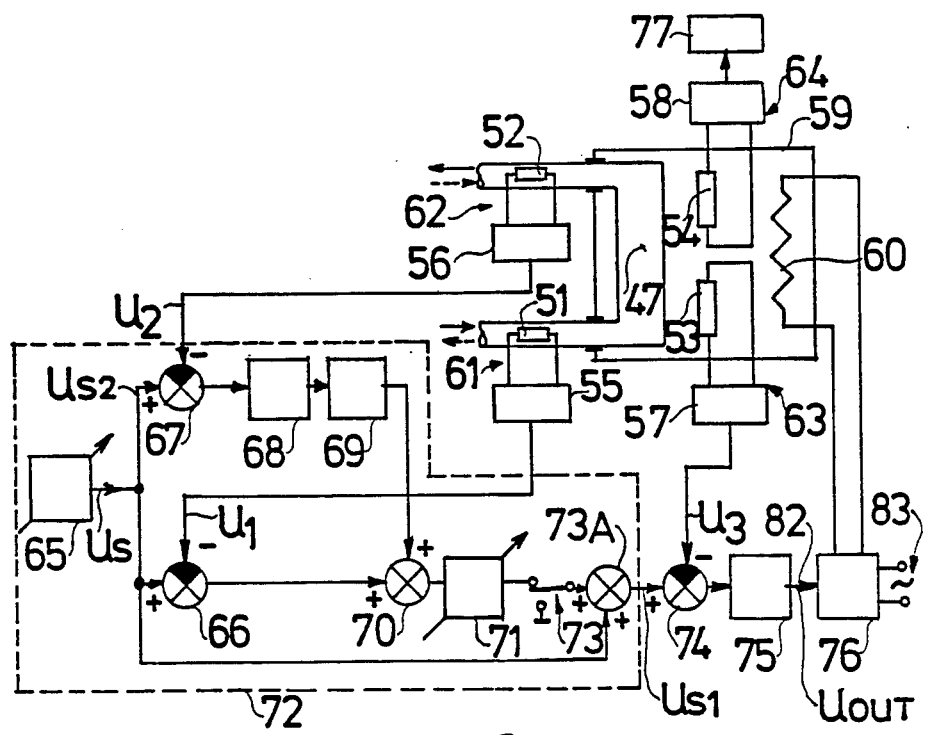
FIG. 2 is a block diagram of a temperature control system of the apparatus according to FIG. 1.

The control according to the invention, of the heating device 59 shown in FIG. 1 is illustrated in FIG. 2. The heating device 59 is provided with a heating element 60, a channel 47 for the fluid to be heated and temperature sensors 53 and 54 arranged between them. A signal converter 57 is connected to the temperature sensor 53 and they together form a transducer 63/signal $U_3$/. A signal converter 58 is connected to the temperature sensor 54 and they together form a transducer 64. The temperature of the fluid entering the channel 57 is sensed by a temperature sensor 51 to which a signal converter 55 is connected and they together form a transducer 61 /signal $U_1$/. The temperature of the fluid flowing out of the channel 47 is sensed by a temperature sensor 52 to which a signal converter 56 is connected and they together form a transducer 62 /signal $U_2$/. If the heating device 59 is of a construction shown in FIGS. 6 to 11, the series-connected heating foil patterns 2 and 102 constitute the heating element 60 /FIGS. 7 and 11/, the series-connected one parts the sensing foil patterns 3 and 103 constitute the temperature sensor 53/ FIGS. 6 and 11/ and the series-connected other parts of the sensing foil patterns 3 and 103 constitute the temperature sensor 54. The temperature sensors 22 and 23 correspond to the temperature sensors 51 and 52, respectively /FIGS. 7 and 8/. The signal converters 55, 56, 57 and 58 may be constituted by resistance bridges supplied by alternating voltage.

The temperature control of the heating device 59 occurs through a control circuit which comprises a difference member 74, a control unit 75, advantageously a PI-regulator, connected to the output of the difference member 74 and a heating element supply unit 76 connected to the output 82 of the control unit 75. The heating element 60 is connected to the output of the heating element supply unit 76. The heating element supply unit 76 receives an alternating voltage of 220 V from mains connection 83 and controls the heating of the heating element 60 in such a manner that once it applies mains voltage to the heating element 60, then it disconnects the heating element 60 from the mains, corresponding to a control signal $U_{OUT}$ at the output 82 of the control unit 75. The heating element supply unit 76 can be a semiconductor thyristor-relay known by itself which performs the switching in and out always at the next zero transition. A reference unit 72 provides a temperature reference value $U_{S1}$ to the positive input of the difference member 74. The output of the transducer 63 is connected to the negative input of the difference member 74.

The reference value unit 72 contains a reference source 65 for setting a signal $U_S$ by means of which the temperature of the heating device 59 corresponding to the prescribed temperature of the fluid can be adjusted. The output of the reference source 65 is connected to positive inputs of difference members 66 and 67, on the one hand, and to an input of an adding member 73A. Therefore, the reference value $U_{S2}$ at the positive input of the difference member 67 is identical with the signal $U_S$. The negative input of the difference member 66 is connected to the output of the transducer 61 and the negative input of the difference member 67 is connected to the output of the transducer 62. The output of the difference member 66 is connected to an input of an adding member 70, whereas the output of the difference member 67 is connected via a control unit 68, advantageously a PID-regulator, and a limiter 69 to the other input of the adding member 70. The output of the adding member 70 is connected through an amplifier 71 with adjustable gain and through a terminal of a change-over switch 73 to the other input of the adding member 73A. The other terminal of the change-over switch 73 is connected to the earthing point. The output of the adding member 73A provides the reference value signal to the positive input of the difference member 74.

The control system operates as follows. In the position shown in FIG. 2 of the change-over switch 73 the filling of the gravity tank 95 takes place in the apparatus according to FIG. 1. The fluid flows, according to the arrow drawn by continuous line, into and from, respectively, the heating device 59, i.e. the transducer 61 measures the temperature of the entering fluid, whereas the transducer 62 the temperature of the discharging fluid going into the gravity tank 95. It is obvious that in this case the difference member 66 provides a signal on its output to the input of the amplifier 71 which signal corresponds to the difference between the prescribed temperature of the discharging fluid and the effective temperature of the entering fluid. The gain of the amplifier 71 is adjusted corresponding to the flow rate and the specific heat of the fluid flowing through the heating device 59, as well as to the parameters of the heating device 59. The amplifier 71 provides a reference value signal at its output to the temperature control circuit of the heating device 59 which signal results in a heating of the device 59 ensuring the prescribed temperature of the discharging fluid. In the case of a definite specific heat and a definite flow rate, the gain of the amplifier 71 can be determined for a given heating device 59 by measurement or by calculation. However, this open-loop setting of the heating of the heating device 59 will not set in a real case the temperature of the discharging fluid accurately to the prescribed temperature, therefore it is advantageous if the difference member 67 compares the output signal of the transducer 62 with a signal proportional to the prescribed temperature and on its output provides a signal corresponding to this difference to an input of the adding member 70 through the control unit 68 and the limiter 69. Thereby, the signal appearing at the output of the difference member 66 and also the reference value signal will continuously vary corresponding to the deviation of the temperature of the discharging fluid from the prescribed temperature. The limiter 69 limits the output signal of the control unit 68 both in positive and in negative directions in order to ensure that the reference value signal set by the difference member 66 could be varied only to a definite extent. This extent is less than ±30%, advantageously less than ±10%. The limitations ensures that in the case of transient procedures, e. g. at the beginning of the temperature control of the fluid, the control system will oscillate in a smaller degree. This control system ensures that the gravity tank 95 can be filled up at a high rate, consequently the period of treatment and the patient's waiting time, respectively, can be rendered shorter, and at the same time the temperature of the fluid entering the gravity tank 95 corresponds substantially to the temperature prescribed for the introduction into the patient.

When the fluid in the gravity tank 95 reaches the prescribed quantity, as indicated by the dynamometer 96, the control unit 87 switches off the heating of the heating element 60, whereas the operation of the roller pump 90 will be temporarily continued. When in the heating device 59 the temperature measured by the transducer 63 decreases to the temperature prescribed for the introduction into the patient, the control unit 87 stops the roller pump 90 and the control system switches over to the value-maintaining control mode. This is symbolized in FIG. 2 by a change-over of the change-over switch 73. Now, the reference value signal is provided directly by the reference source 65. Hereupon, in specific cases with the intermediation of a waiting pause, the introduction of the fluid into the patient from the gravity tank 95 begins. In FIG. 2 the fluid flows, corresponding to the arrow drawn with dotted line, through the heating device 59 in which parts near the fluid flowing in the channel 47 are set to the prescribed temperature of the fluid. This is ensured in such a way that the temperature sensor 53 is located at these parts as shown with the sensing foil patterns 3 and 103/FIG. 11/.

The sensing foil patterns 3 and 103 provide for two independent temperature sensors. One of them is the temperature sensor 53, the other is the temperature sensor 54. The output of the transducer 64 including the temperature sensor 54 is connected to a switch-off and alarm unit 77 which is for switching off the apparatus and for providing an alarm signal when the temperature in the heating device 59 rises above the prescribed value for whatever reason, e. g. in the case of a breakdown. This switchingoff is effected by the control unit 87 in the case of the apparatus according to FIG. 1. Would this dangerous situation happen to come during the introduction of the fluid into the patient, the introduction is broken off by closing the valve 92, and by opening the valve 93 the fluid flows into the lower collecting tank 98.

Figure 3:
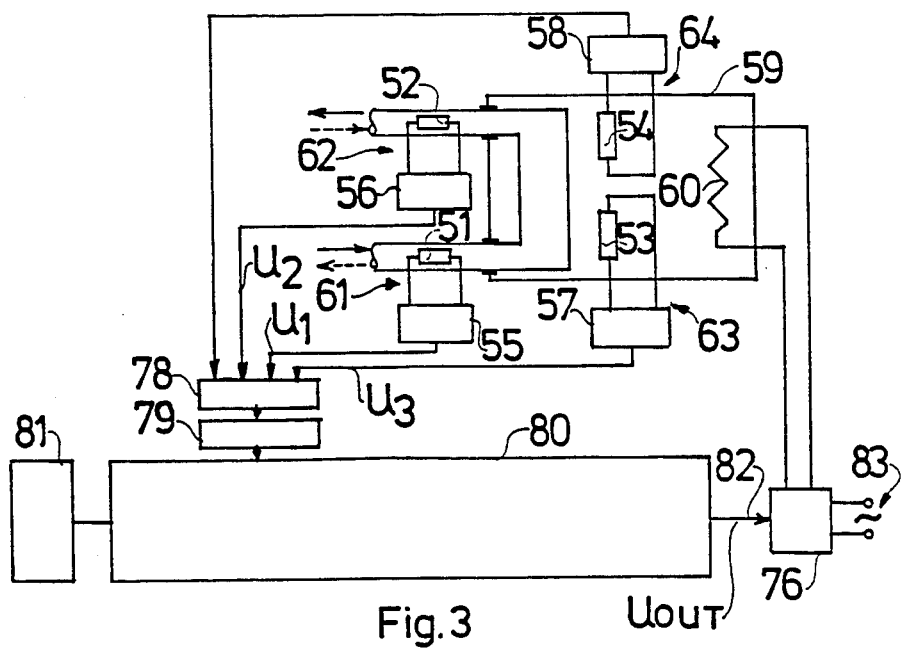
FIG. 3 is a block diagram of another embodiment of the temperature control system of the apparatus according to FIG. 1.

An advantageous embodiment of the temperature control system of the heating device 59 is illustrated in FIG. 3. In the case of this embodiment, the temperature control is made in digital way. The outputs of the transducers 61, 62, 63 and 64 are connected through a scanner 78 to the input of an analog-digital converter 79, the output of which is connected to a digital data processing device 80. The data processing device 80 is provided with an operating and indicating unit 81 and has an output 82 controlling the heating element supply unit 76. The data processing device 80 is advantageously realized with a microprocessor and programmed so that it carries out the control according to FIG. 2.

Figure 4:
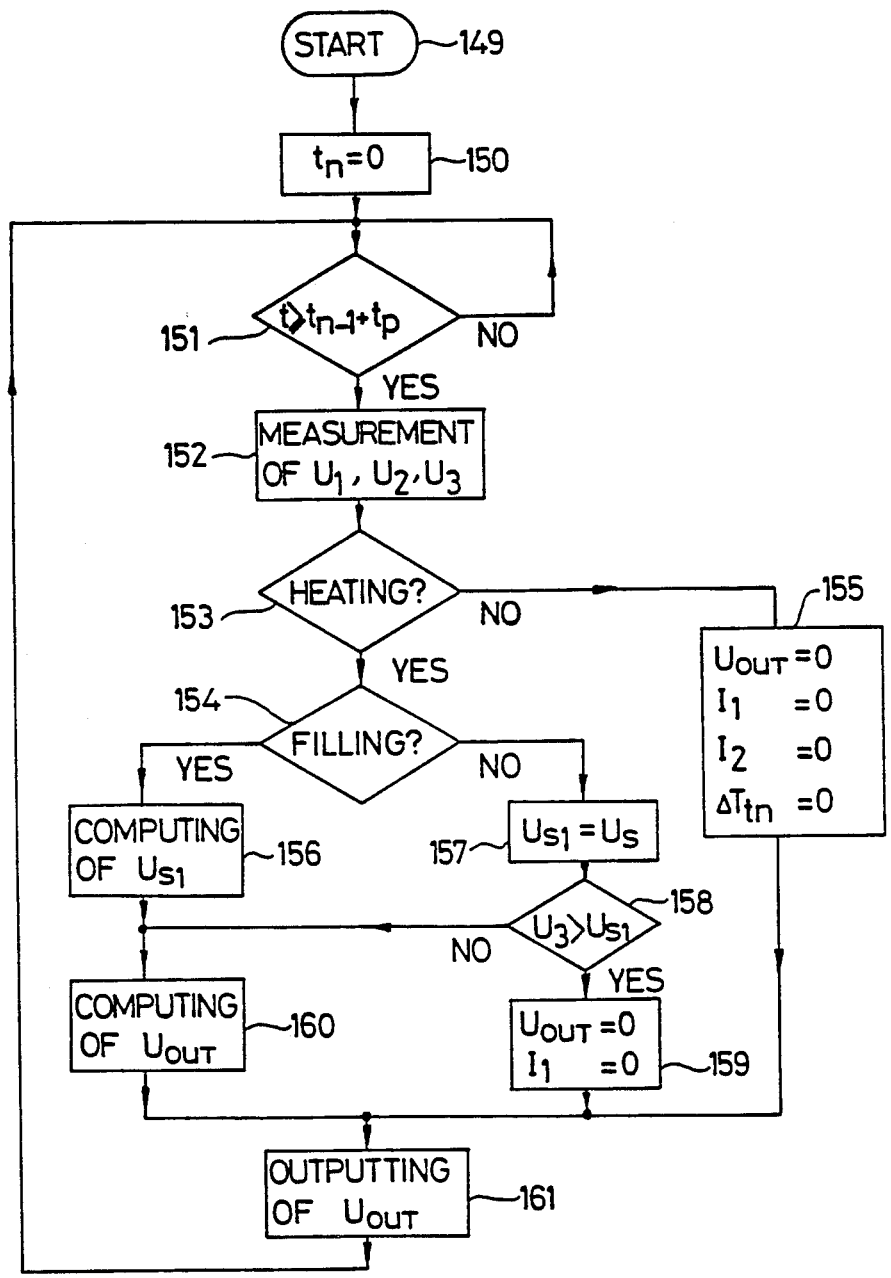
FIG. 4 is a flow chart of the temperature control program of the system according to FIG. 3.

In FIG. 4 a flow chart of the control program of the data processing device 80 is shown by way of example. The start of the program in step 149 occurs by switching in the apparatus and the time t begins at this moment. In step 150 the initial value $t_n=0$ is set, in step 151 follows the waiting for the expiration of a period $t_p$. The control program repeats itself in periods $t_p$. When the period $t_p$ elapses, in step 152 the signals $U_1$, $U_2$ and $U_3$ of the transducers 61, 62 and 63, being proportional to the appropriate temperatures, are scanned and read-in. In step 153 it is checked whether the heating of the heating device 59 is necessary. Immediately following the start, this is not yet necessary, therefore in step 155 the setting of $U_{OUT1}=0$ as well as that of the initial values of parameters $\Delta T_{tn}$, $I_1$ and $I_2$ occur, said parameters being explained below. In the next step 161 a control signal $U_{OUT}=0$ is sent to the output 82. Thereafter, the program repeats itself after the expiration of a period $t_p$.

If the heating proves to be necessary in step 153, in step 154 it is examined whether the filling of the gravity tank 95 occurs. If so, in step 156 the reference value $U_{S1}$ determining the temperature of the heating device 59 is calculated as follows:

$$U_{S2} = U_S + C_2 /U_3 - U_2/ \qquad /1/$$

$$\Delta T_{tn} = U_{S2} - U_2 \qquad /2/$$

$$I_2 = I_2 + K_2 \Delta T_{tn} \qquad /3/$$

$$L_2 = \text{limitation } /I_2, I_{2max}, I_{2min}/ \qquad /4/$$

$$U_{S1} = P_2 \Delta T_{tn} + I_2 + D_2 / \Delta T_{tn} - \Delta T_{tn-1}/ + C_1/U_{S2} - U_1/ + U_S \qquad /5/$$

where $C_2$, $K_2$, $I_{2min}$, $I_{2max}$, $P_2$, $D_2$ and $C_1$ are constants.

The reference value $U_{S2}$ will be calculated according to the relationship /1/ which deviates from the control system according to FIG. 2 in so far as a correction member proportional to the difference between the temperature /$U_3$/ measured in the heating device 59 and the temperature /$U_2$/ of the discharging fluid is also taken into consideration. In a measuring arrangement, e. g. according to FIGS. 7 and 8, where the temperature sensor 23 is heat-insulated from the heated supporting plate 1 by means of a teflon ring 20, the signal $U_2$ of the transducer 62 is somewhat higher than the value which would correspond to the temperature of the discharging fluid, due to the warmer heating device 59. This error of measurement is compensated by the increase of the reference value $U_{S2}$.

According to the relationship /2/, a value for the computation of the proportional and differential components of the per se known PID control algorithm corresponding to the control unit 68 of FIG. 2 is calculated. The integrating component is calculated according to the relationship /3/ which component is limited according to the relationship /4/, corresponding to the limiter 69 of FIG. 2. According to the relationship /5/, the reference value $U_{S1}$ is calculated from the proportional /P/, integrating /I/ and differential /D/ components and from the components $C_1/U_{S2} - U_1/$ and $U_S$, corresponding to the adding members 70 and 73A of FIG. 2.

Hereupon, the value of the control signal $U_{OUT}$ will be calculated in step 160, as follows:

$$I_1 = I_1 + K_1/U_{S1} - U_3/ \qquad /6/$$

$$U_{OUT} = P_1/U_{S1} - U_3/ + I_1 \qquad /7/$$

$$U_{OUT} = \text{limitation } /U_{OUT}, U_{OUTmin}, U_{OUTmax}/ \qquad /8/$$

where $K_1$, $P_1$, $U_{OUTmin}$ and $U_{OUTmax}$ are constants.

According to the relationship /6/, the integrating component of the per se known PI control algorithm is calculated, corresponding to the control unit 75 of FIG. 2. According to the relationship /7/, the value of the control unit $U_{OUT}$ is calculated, which is limited according to the relationship /8/. E. g. the constants $U_{OUTmin}$ and $U_{OUTmax}$ correspond to 0 and 5 volts, respectively. The control signal $U_{OUT}$ determined in this way will be sent to the output 62 in step 161.

When at the step 154 not the filling of the gravity tank 95 occurs but there is the introduction into the patient or the waiting before the introduction, the control algorithm is different. In step 157 the reference value $U_{S1}$ is set to $U_S$, corresponding to the other position of the change-over switch 73 in FIG. 2. In step 158 it is checked whether the temperature of the heating device 59 is higher than the temperature determined by the reference value $U_{S1}$. If so, in step 159 $U_{OUT} = 0$ and $I_1 = 0$ will be set and in step 161 a control signal $U_{OUT} = 0$ will be output. Otherwise, i.e. if the heating device 59 is cooled down so that it has to be heated, the control signal $U_{OUT}$ will be calculated in step 160 described above and output in step 161.

Evidently, the data processing device 80 can perform an addition also other tasks, thus e. g. it can execute also the task of the switch-off and alarm unit 77 illustrated in FIG. 1. The temperature control system can be realized, however, also in analog manner, through an analog realization of the elements illustrated in FIG. 2.

In FIG. 5 an other advantageous control system of the heating device of the apparatus according to FIG. 1 is shown. The reference signs correspond to the reference signs of FIG. 2, therefore only the differences are explained here. The control system according to FIG. 5 departs from the control system of FIG. 2 in that the reference value signal corresponds here not to a definite temperature in the heating device 59 but to a definite heat flux directed to the fluid flowing in the channel 47. For this purpose, two temperature sensors 53A and 53B are arranged on two placed behind each other in the direction of the heat flux. The temperature sensor 53A constitutes together with a signal converter 57A a transducer 63A, whereas the temperature sensor 53B together with a signal converter 57B a transducer 63B. The output of the transducer 63A is connected to the positive input of a difference member 48, whereas the output of the transducer 63B is connected through a change-over switch 49 to the negative input of the difference member 48. The output of the difference member 48 is connected to the negative input of the difference member 74. The output of the difference member 74 is connected through the control unit 75 to the input of the heating element supply unit 76 which supplies the heating element 60, e. g. with a direct current. If the heating device 59 is constructed as shown in FIGS. 6 to 11, the series-connected heating foil patterns 2 and 102 /FIGS. 7 and 11/ correspond to the heating element 60, whereas the series-connected one parts of the sensing foil patterns 3 and 103 /FIGS. 6 and 11/ to the temperature sensor 53A. The series-connected heating foil patterns 2 and 102 themselves may constitute the temperature sensor 53B. The bridge measurement of the resistance at an alternating voltage of a few kHz can be easily separated from the direct current heating. However, the temperature sensor 53B may be constructed so that beside the heating foil patterns 2 and 102 another sensing meander configuration is formed on the same side of the supporting plates 1 and 101, respectively, in the same manner as the meander configurations 4 and 4A reaching mutually into each other /FIG. 6/.

A further difference as compared to FIG. 2 consists in the measurement of the flow rate of the fluid entering the gravity tank 95 when filling, by means of a flow rate sensor 51A and a signal converter 55A, the output of which is connected to a control input of the amplifier 71. Thereby the gain of the amplifier 71 is controlled so that a greater gain belongs to a greater flow rate. However, the control system according to FIG. 5 can function even without this flow rate measurement.

The control system according to FIG. 5 controls the temperature of the fluid while the change-over switches 49 and 73 are in the indicated positions during the filling up of the gravity tank 95. Now, the fluid flows through the channel 47 in the direction of the arrow drawn with continuous line. The output signal of the difference member 48 is proportional to the difference between the temperatures measured by the temperature sensors 53B and 53A and thus to the heat flux flowing from the heating element 60 to the fluid. The reference value signal shall be set in the reference unit 72 by the amplifier 71 in such a manner that the corresponding heat flux increases the temperature of the entering fluid until its discharge—in the case of a definite flow rate—to the prescribed temperature. During the introduction from the gravity tank 95 into the patient—when the fluid flows according to the dotted arrow—the change-over switches 49 and 73 are in the other position. Thus, this control system functions just in the same manner as that according to FIG. 2, since the temperature sensor 53B is switched off and the temperature sensor 53A corresponds to the temperature sensor 53.

Although in FIGS. 1 to 5 a peritoneal dialysis apparatus was disclosed, the invention can be used for the introduction of whatever physiological fluid, e. g. blood or infusion solution.

Figure 6:
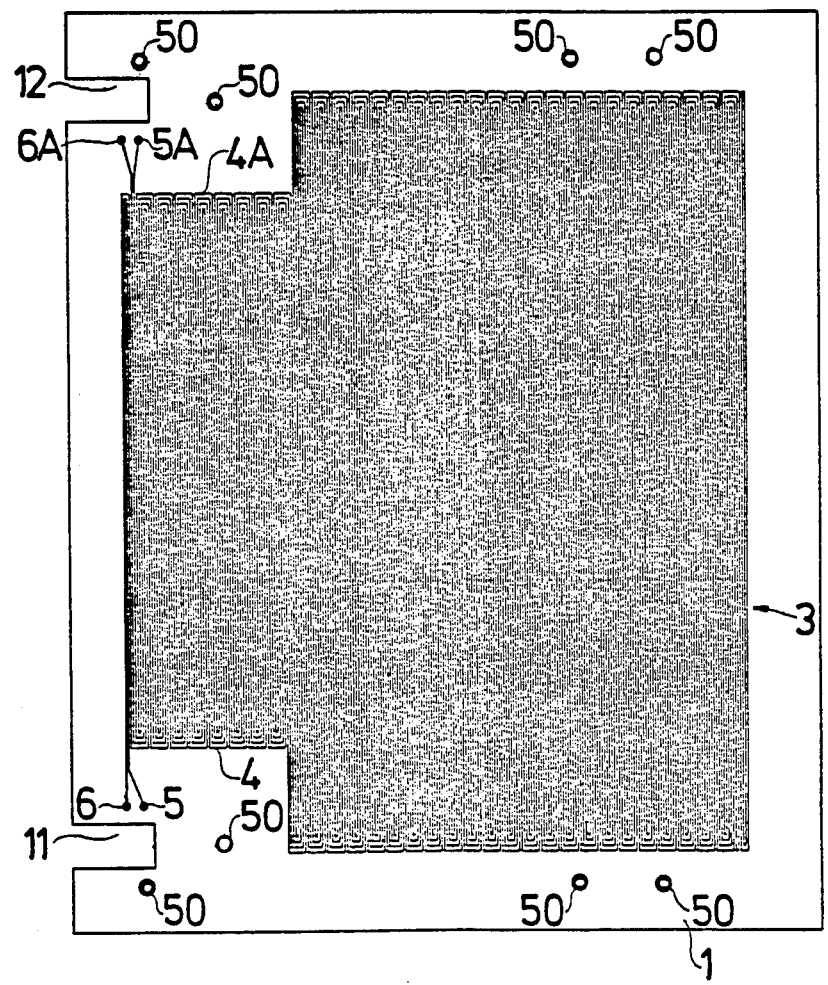
FIG. 6 is a view of one side of a supporting plate provided with a sensing foil pattern, arranged in one side wall of the heating device according to the invention.

In FIGS. 6 to 8 a side wall 28 of a heating device well applicable in the apparatus according to the invention, and a supporting plate 1 of the side wall 28 are shown. On one side of the supporting plate 1 made of an insulating material /FIG. 7/ a heating foil pattern 2 constituting a meander configuration is formed to the ends of which current inlet plates 9 and 10 are connected. On the other side of the supporting plate 1 /FIG. 6/ a sensing foil pattern 3 constituting two meander configurations 4 and 4A is formed which serves as two temperature sensing resistances. The meander configuration 4 has endings 5 and 6, whereas the meander configuration 4A endings 5A and 6A. It is to be seen in FIG. 6 that the two meander configurations 4 and 4A reach comb-like into each other and cover almost uniformly the surface of the supporting plate 1. The heating foil pattern 2 on the other side of the supporting plate 1 constitutes similarly a meander configuration which covers almost uniformly the surface of the supporting plage 1 so that a practically uniform heating of the supporting plate 11 is ensured. The meander configuration of the heating foil pattern 2 and those of the sensing foil pattern 3 are arranged perpendicularly to each other, in order to keep the inductive coupling at the lowest possible value, on the one hand, and to provide for a better temperature sensing, on the other hand. This arrangement renders possible a highly accurate detection of the average temperature of the surface of supporting plate 1 irrespective of the relative position of the heating foil pattern 2 and the sensing foil pattern 3. The heating foil pattern 2 can be advantageously supplied from the mains voltage and the meander configurations 4 and 4A of the sensing foil pattern 3 can be connected to bridge circuits each of them supplied with a voltage of higher frequency than that of the mains voltage, e. g. of a few kHz.

The heating foil pattern 2 is very thin, consequently its heat transmitting surface is large as compared to its cross section, therefore it ensures a high surface power density. The cross section shall be chosen so that the required heating power should be ensured with the available supply voltage. In an advantageous embodiment the meander configuration is made of a 35 μm thick copper foil where the width of the straight foil sections is 0.7 mm, the resistance of the entire heating foil pattern amounts to 24 ohm, the heating voltage is 110 V and the heating power is 400 W. If two heating foil patterns 2 are connected in series in a heating device, the heating device can be supplied from a mains voltage of 220 V. For control purposes the heating power must be, of course, controllable.

The sensing foil pattern 3 may be similarly made of a 35 μm thick copper foil where the width of the straight foil sections is 0.35 mm, whereas the resistance is 2×50 ohm. This construction provides for a double temperature sensor which may be necessary for medical devices due to safety regulations. In some cases, a sensing foil pattern 3 constituting one single temperature sensor may be sufficient.

The heating foil pattern 2 can also be used, if desirable, as a sensing foil pattern, e. g. in such a manner that the heating is effected by a D. C. voltage while the sensing of the temperature /resistance measurement/ occurs in a measuring bridge supplied by an alternating voltage. It is also possible to arrange a further sensing foil pattern beside the heating foil pattern 2, e. g. in such a way that two meander configurations are electrically separated from each other, but, similarly to the sensing foil pattern 3, they reach comb-like into each other. This solution has a significance if the temperature should be measured on both sides of the insulating supporting plate 1, e. g. for the measurement and control of the heat flux according to FIG. 5.

The arrangement ensures that the sensing foil pattern 3 measures substantially the average temperature of the entire surface of the supporting plate 1. The endings 5, 6 and 5A, 6a are led through to the other side of the supporting plate 1 through metal-coated borings and are coupled there to soldering points 7, 8 and 7A, 8A by means of foil sections. The electric connections both to the heating foil pattern 2 and to the sensing foil pattern 3 can be ensured from the side shown in FIG. 7. On the side provided with sensing foil pattern 3 of the supporting plate 1 /FIG. 6/ small foil rings 50 are formed which mark the positions of borings 50A shown in FIG. 7 and of the temperature sensors 22 and 23. The supporting plate 1 is provided with two notches 11 and 12 serving for the arrangement of inlet opening and output opening of the bag 26 to be described later in connection with FIG. 10.

The supporting plate 1 can be made of a printed circuit board of about 1.5 mm thickness, coated on two sides with foil and reinforced with glass fiber, and the foil patterns can be produced with an etching technology usual with printed circuit boards. These common printed circuit plates can be used if the temperature of the heating foil pattern 2 is not higher than 100° C. For a higher temperature another supporting plate 1 provided with a heating foil pattern 2 is required. E. g. a conducting foil applied in thin layer onto a ceramic may be suitable. The foil patterns applied to the two sides of the supporting plate 1 can be made of different materials. It is advantageous if the resistance of the heating foil pattern 2 is only slightly dependent on the temperature. The sensing foil pattern 3, however, shall be expediently made of a material having a temperature dependence as high as possible. The foil patterns can be applied to the supporting plate 1 by vacuum evaporation.

In FIGS. 7 to 9 the side wall 28 is shown in assembled state. It is to be seen in FIG. 9 that to one side of the supporting plate 1 the heating foil pattern 2 is applied, provided with a protective layer 14 which protects the heating foil pattern 2 against oxydation and external effects and at the same time constitutes an insulating layer. The protective layer 14 may be e. g. a transparent solder laquer coat usual in the printed circuit technology, having a thickness of about 0.05 mm. To the other side of the supporting plate 1 the sensing foil pattern 3 is applied, on which a temperature equalizing layer 13 is fixed by an adhesive insulating layer 15. The temperature equalizing layer 13 shall be made of a material of good thermal conductivity, e. g. of aluminum or copper. The thickness of the temperature equalizing layer 13 shall be chosen so that it can equalize the temperature differences arising due to the construction and position of the heating foil pattern 2 and to the inhomogenity in the thermal conductivity of the medium to be heated without, however, unduly increasing the heat capacity of the heating device. In the embodiment shown an aluminum plate of 0.5 mm thickness is appropriate. The insulating layer 15 may consist e. g. of polyester resin strengthened with glass fiber, having a thickness of about 0.1 mm which can be pressed to the side covered with the sensing foil pattern 3 of the supporting plate 1 at a temperature of approx. 170° C. This fastening process may be applied up to an operating temperature of about 120° C.

FIG. 10 illustrates a view of the side wall 28 seen with the side of the temperature equalizing layer 13, provided with a bag 26 laid onto the temperature equalizing layer 13. The fluid to be heated by the heating device flows in a meander shaped channel 47 formed in the bag 26. The channel 47 is connected to an inlet opening 45 as well as to an outlet opening 46. The bag 26 can be made of two plastic foils by welding and pipes welded in between the two plastic foils form the inlet opening 45 and the outlet opening 46. For clamping these pipes, cylindrical embossings 16 and 17 are made in the temperature equalizing layer 13. The positioning of the bag 26 is ensured by openings made on the bag 26 so as to coincide with the borings 50A in points corresponding to the small rings 50. For measuring the temperature of the fluid entering the bag 26 a calotte-shaped metal plate 19 is engaged in a teflon ring 18 fastened in the supporting plate 1, and on the side of the metal plate 19 which is opposite to the bag 26, a temperature sensor 22 is arranged. The temperature sensor 22 may be e. g. a platinum heat resistance provided with terminals 24. It is to be seen in FIG. 7 that the teflon ring 18 is arranged at a suitable distance from the heating foil pattern 2. Its purpose is to provide for a good heat insulation between the metal plate 19, on the one hand, and the supporting plate 1 as well as the temperature equalizing layer 13, on the other hand. For the measurement of the temperature of the fluid discharging from the bag 26 a metal plate 21 provided with temperature sensor 23 is engaged in a similar teflon ring 20. The temperature sensor 23 has terminals 25. The layout is fully symmetrical, therefore the flow direction of the fluid determines which of the temperature sensors 22 and 23 will measure the temperature of the entering fluid and which of them the temperature of the discharging fluid. The metal plates 19 and 21 can be produced of e. g. anodically oxidized aluminum of 13 mm diameter and 0.3 mm thickness. On the back side a platinum heat resistance applied on a small ceramic plate of 1 mm$^2$ can be glued.

Figure 11:
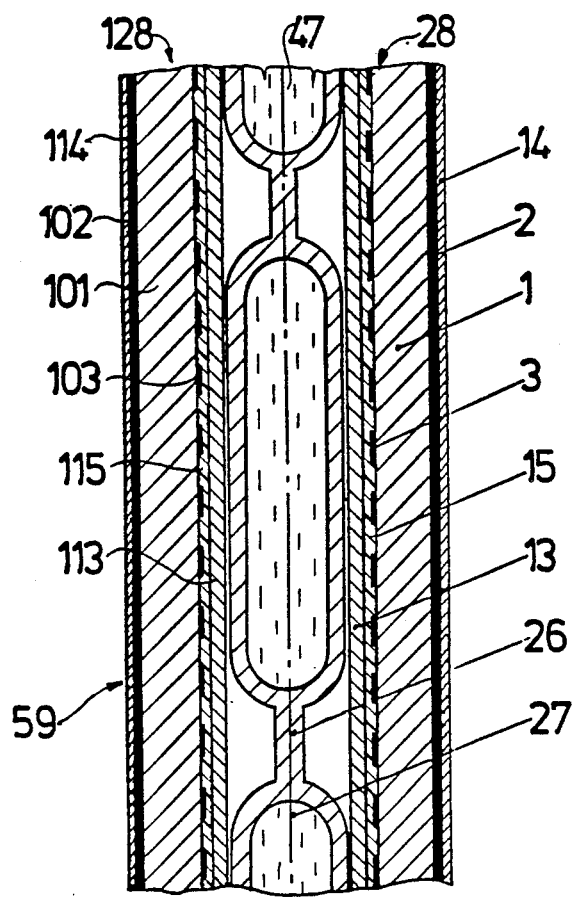
FIG. 11 is a schematic partial sectional view of the heating device according to the invention.

In FIG. 11 a part of the two side walls 28 and 128 of the heating device 59, as well as a part of the bag 26 arranged between the side walls 28 and 128 are shown. The fluid 27 to be heated flows in the bag 26 in a meander-shaped channel 47. The reference signs of the elements of the side wall 128 correspond to the reference signs used at the side wall 28 with the difference that they are higher by 100. No temperature sensors for the fluid entering the bag 26 and discharging from the bag 26 are built in into the side wall 128, otherwise the construction corresponds to that of the side wall 28.

Figure 12:
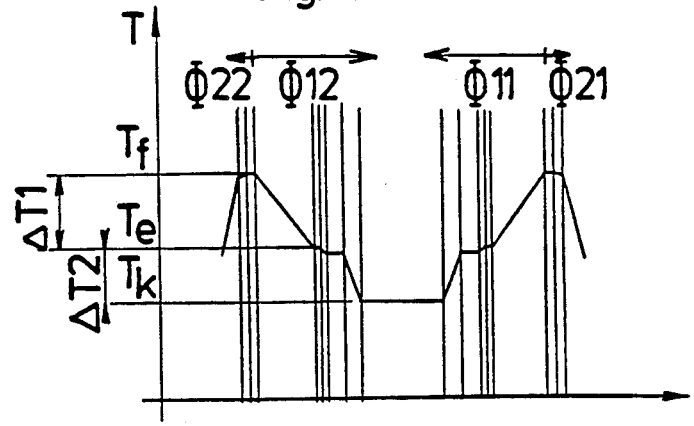
FIG. 12 is a diagram indicating the temperature conditions in the heating device according to FIG. 11.

FIG. 12 illustrates the temperature conditions in the heating device 59 according to FIG. 11. The diagram shows the average value of the temperature T obtained in the various layers of the heating device 59. It is apparent that the highest temperature $T_f$ is achieved at the heating foil patterns 2 and 102. From there heat fluxes Q11 and Q12 flow to the fluid 27, on the one hand, and heat fluxes Q21 and Q22 flow outwards, on the other hand, causing a loss. Due to the temperature drop in the supporting plates 1 and 101, the sensing foil patterns 3 and 103 sense an average temperature $T_e$. Between the temperatures $T_f$ and $T_e$ there is a temperature difference $\Delta T1$. A small temperature step arises in each of the insulating layers 15 and 115, whereas in the temperature equalizing layers 13 and 113 practically no temperature step occurs. It is obvious that the temperature of the temperature equalizing layers 13 and 113 corresponds practically to the temperature $T_e$. A further temperature drop occurs in the plastic wall of the bag 26 and, in accordance therewith, the fluid 27 is an average temperature of $T_k$. Between the temperatures $T_e$ and $T_k$ there is a temperature difference $\Delta T2$.

In the heating device 59 according to FIG. 11 the sensing foil patterns 3 and 103 sense the average temperature relating to the entire side wall 28 and 128, respectively. The effective temperatures along the sensing foil patterns 3 and 103 are determined according to the fact what a heat extraction is caused by the fluid flowing in the channel 47 at different points of the supporting plates 1 and 101, respectively. Correspondingly, the temperature increases constantly from the inlet point to the outlet point of the fluid. In the streaming fluid, however, instabilities of flow and also bubbles can occur and the latters, being stuck in the meander-shaped channel 47, cause local heating-up. In order to prevent this phenomenon, temperature equalizing layers 13 and 113 are provided for protecting both the bag 26 and the side walls 28 and 128.

Figure 13:
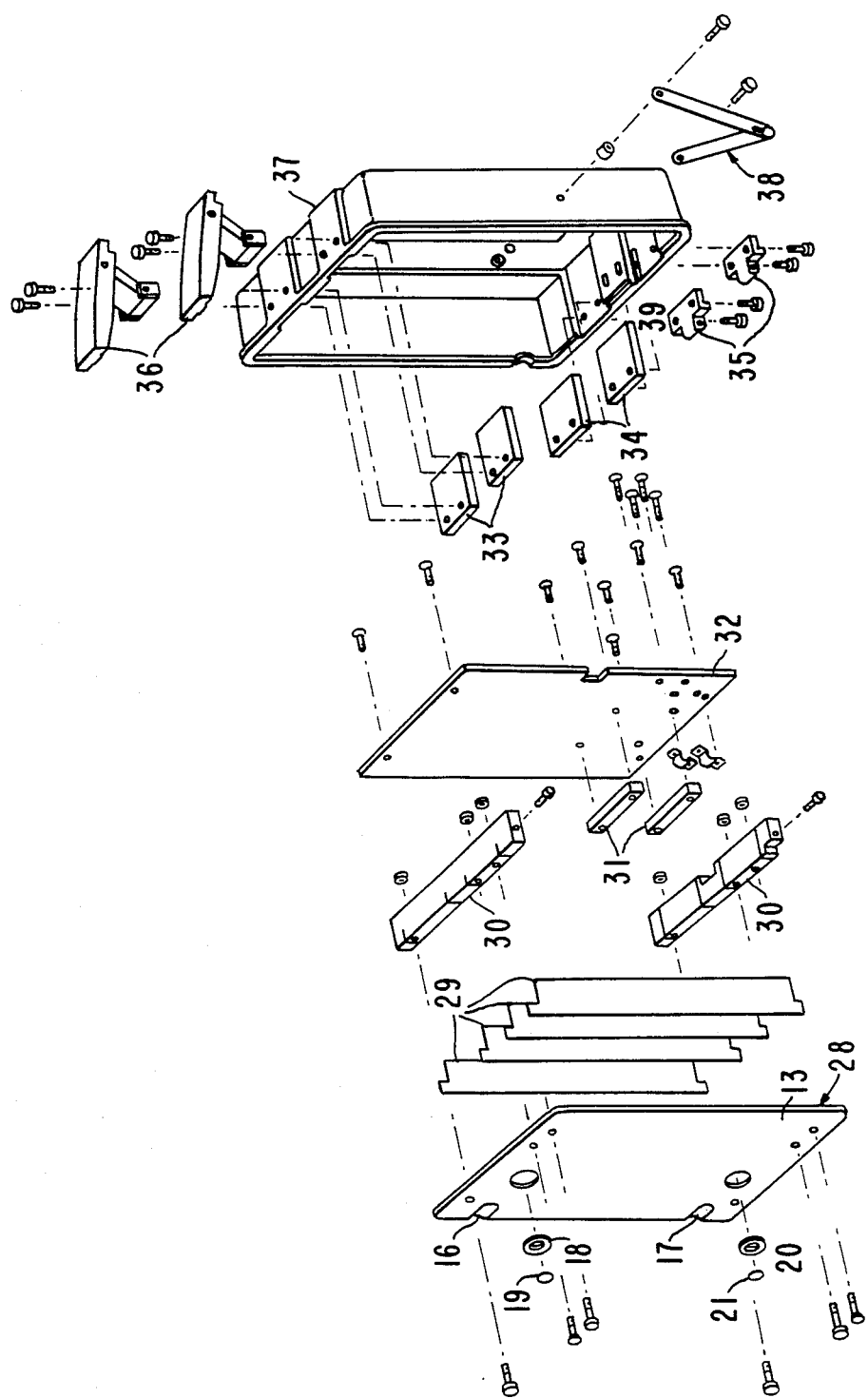
FIG. 13 is an exploded perspective view of one side wall of an exemplary heating device and FIG. 14 is an exploded perspective view of the other side wall of the heating device according to FIG. 13.
Figure 14:
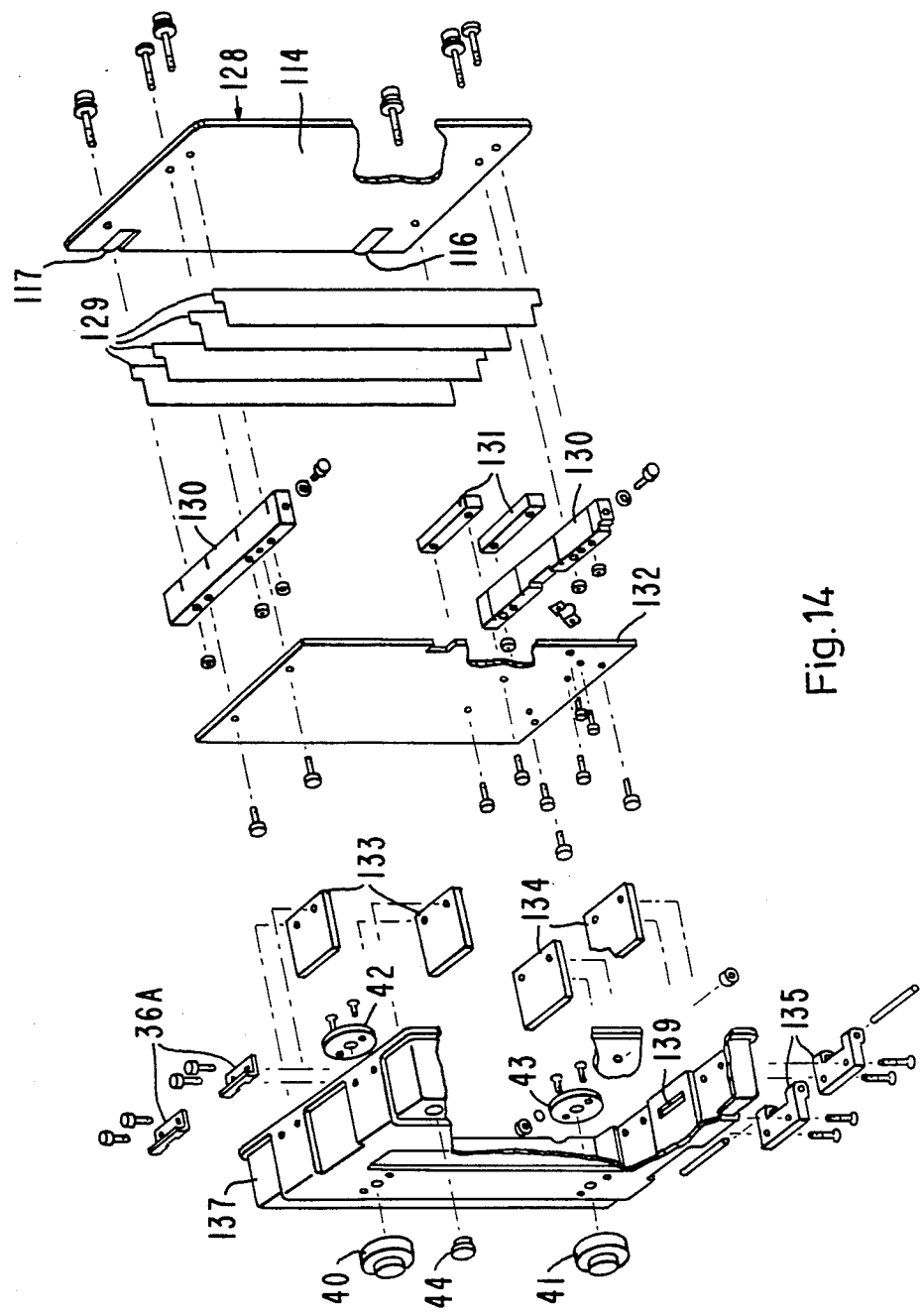

In FIGS. 13 and 14 armatures are shown each of them comprising a side wall 28, 128, respectively, of the heating device 59. The side wall 28 /FIG. 13/, reinforcing ribs 29 made of an insulating material, retainers 30 and a mounting plate 32 of printed circuit are fastened to each other by means of screws. One of the reinforcing ribs 29 is provided with a printed circuit and resistances of bridge signal converters belonging to the temperature sensing foil pattern 3, as well as to the temperature sensors 22 and 23 arranged on the metal plates 19 and 21, respectively. A releasable connector closing at the assembly of the armature is provided for electric connection, one half of which is fastened to the reinforcing rib 29 provided with the printed circuit, the other half to the mounting plate 32 provided with printed circuit. This device is arranged when assembled in a casing 37 made of a plastic material and is fastened e. g. at the flange by gluing in such a manner that the flange of the casing 37 and the external surface of the temperature equalizing layer 13 of the side walls 28 are in the same plane. There is an opening 39 on the bottom part of the casing 37 through which a ribbon cable providing for the electric connection is introduced. The end of the cable is soldered to the mounting plate 32 provided with printed circuit and is fastened thereto with clamping elements 31. To the bottom part of the casing 37 hinges 35 are fastened by means of retaining plates 34 and screws, whereas above two eccentric locks 36 are fastened by means of retaining plates 33 and screws.

The hinges 35 of the casing 37 join hinges 135 of the casing 127 fixed by means of retaining plates 134 /FIG. 14/, and they render it possible that the two casings 37 and 137 are tiltable as compared to each other, at most to an extent permitted by a distance element 38, e. g. to 90°. In the casing 137 there is a mounting unit consisting of the side wall 128, reinforcing ribs 129, retainers 130 and a mounting plate 132 provided with printed circuit which are similarly fastened to each other by screws. In the upper part of the casing 137 tongues 36A are fixed by means of retaining plates 133. The eccentric locks 36 are linked with these tongues 36A in the closed position of the two casings 37 and 137, and in this position there is a gap of several mm between them for the arrangement of a bag flown through by the fluid to be heated. The electric connection of the side wall 128 is made in the same way as that of the side wall 28, the ribbon cable enters through an opening 139 formed in the bottom part of the casing 137 and the ribbon cable is connected to the mounting plate 132 by clamping elements 131. Fastening buttons 40 and 41 are secured to the casing 137 by means of disc-chaped retaining plates 42 and 43 and screws. The fastening buttons 40 and 41 serve for the fastening of the complete heating device 59. On the casing 137 there is a heating indicator 44, too which lights in the case when the heating foil patterns 2 and 102 of the side walls 28 and 128 are switched on.

The embodiment of the heating device 59 shown in FIGS. 11, 13 and 14 is especially advantageous for medical use where the sterility of the physiological fluid shall be ensured also after flowing through the heating device 59. The invention is, however, not restricted to this embodiment. It is easy to see that the limiting walls of the channel 47 arranged between the side walls 28 and 128 may be constituted by the temperature equalizing layers 13 and 113. Between the temperature equalizing layers 13 and 113 a e. g. meander-shaped channel made of metal may be formed, providing for a very good heat transfer to the fluid 27. In some cases, the temperature equalizing layers 13 and 113 may also be omitted, and the insulating layers 15 and 115 may be used as limiting walls of the channel 47. In this case, the temperature equalization occurs through the fluid flowing in the channel 47.

I claim:

1. A method for introducing a physiological fluid into a human or animal organism at a prescribed temperature, wherein the fluid is pumped through a controlled heating device into a gravity tank and then introduced from the gravity tank through the same heating device into the organism by gravity, characterized in that during the pumping into the gravity tank the temperature of the fluid entering the heating device is measured and, on the basis of the measured temperature, a temperature or a heat flux causing substantially the prescribed temperature of the fluid discharging from the heating device is set in the heating device, and that during the introduction by gravity the temperature of the heating device is controlled to the prescribed temperature of the fluid.

2. The method according to claim 1, characterized in that during the pumping into the gravity tank the temperature of the fluid discharging from the heating device is also measured, and said temperature or heat flux set in the heating device is varied according to the difference between the prescribed temperature and the measured temperature of the discharging fluid.

3. The method according to claim 1, characterized in that during the pumping into the gravity tank said temperature in the heating device is set so that an average temperature of parts of the heating device that are near the fluid is measured and a first signal proportional to this average temperature is produced, and that the first signal is compared to a second signal determined on the basis of the temperature of the entering fluid, and the heating of the heating device is controlled according to the difference between the first and second signals.

4. The method according to claim 3, characterized in that during the pumping into the gravity tank the temperature of the fluid discharging from the heating device is also measured, and that said second signal is varied proportional to the difference between the prescribed temperature and the measured temperature of the discharging fluid at most by ±30%, preferably at most by ±10%.

5. The method according to claim 1 or claim 2, characterized in that during the pumping into the gravity tank the quantity of the fluid in the gravity tank is measured and when this quantity reaches a predetermined value, the heating of the heating device is switched off but the pumping is continued and the temperature of the heating device is continuously measured, and if the temperature of the heating device drops to the prescribed temperature of the fluid, the pumping is finished and until starting with the introduction by gravity the temperature of the heating device is controlled to the prescribed temperature of the fluid.

6. The method according to claim 3 or claim 4, characterized in that during the introduction by gravity said temperature control of the heating device is carried out so that the average temperature of the parts of the heating device that are near the fluid is measured and a first signal proportional to this average temperature is produced, this first signal is compared to a third signal corresponding to the prescribed temperature and the heating of the heating device is controlled according to the difference between the first and third signals.

7. The method according to one of claims 1 to 4, characterized in that during the introduction by gravity the average temperature of the parts of the heating device that are near the fluid is measured also independently of the temperature control of the heating device, and above a predetermined average temperature value the introduction is broken off and an alarm signal is produced.

8. An apparatus for introducing a physiological fluid into a human or animal organism at a prescribed temperature, comprising a pump for delivering the physiological fluid through a heating device provided with a control system into a gravity tank and a duct for introducing the fluid from the gravity tank through the same heating device into the organism, characterized in that said control system of the heating device comprises a control circuit for setting the temperature or the heat flux in the heating device and for said control circuit a reference unit producing a varying reference value altering proportionally to a measured temperature of the fluid entering the heating device during the delivery into the gravity tank and a constant reference value for maintaining the heating device at the prescribed temperature of the fluid during the introduction into the organism, and that an input of said reference unit is connected to an output of a first transducer measuring the temperature of the fluid entering the heating device.

9. The apparatus according to claim 8, characterized in that said reference unit has also another input connected to an output of a second transducer measuring the temperature of the fluid discharging from the heating device, and that said reference unit comprises means for superimposing a signal corresponding to the difference between the prescribed temperature of the fluid and the measured temperature of the discharging fluid onto said varying reference value.

10. The apparatus according to claim 9, characterized in that said control circuit comprises a third transducer measuring the average temperature of parts of the heating device that are near the fluid and a unit supplying a heating element of the heating device on the basis of the difference between the reference value and the signal of the third transducer.

11. The apparatus according to claim 10, characterized in that said control system comprises a digital data processing device connected to the first, second and third transducers, said digital data processing device having an output controlling said unit supplying the heating element.

12. The apparatus according to claim 10 or claim 11, characterized in that said heating device comprises two heated side walls and a flat bag arranged therebetween, said bag being provided with an inlet opening and an outlet opening for the fluid, that each of said walls comprises a supporting plate made of an electrically insulating material, a heating foil pattern made of a conductive material on a side of the supporting plate, which side is opposite to the bag, and a temperature sensing foil pattern made of a conductive material on a side of the supporting plate, which side is towards the bag, and that each temperature sensing foil pattern is covered with an insulating layer and on that with a temperature equalizing layer made of a heat conducting material, wherein the heating foil patterns constitute said heating element, while at least a part of the sensing foil pattern constitutes a temperature sensor of said third transducer.

13. The apparatus according to claim 12, characterized in that the heating foil patterns of said two side walls are electrically in series connected, and that the said parts of the sensing foil patters of said two side walls are similarly series connected.

14. The apparatus according to claim 12, characterized in that each of said first and second transducer comprises on one of said supporting plates a metal plate fastened heat-insulated at the inlet opening and at the outlet opening of the bag, respectively, and a temperature sensor on a side of the metal plate, which side is opposite to the bag.

15. The apparatus according to claim 12, characterized in that at least another part of the sensing foil pattern constitutes a temperature sensor of a fourth transducer, and that there is a unit switching off the apparatus and producing an alarm signal, said unit being connected to the fourth transducer.

16. A method for controlling the temperature of a flowing medium, comprising the steps of:
    causing the medium to flow through a heating device having a heating element,
    measuring the temperature of the medium entering the heating device,
    measuring the temperature of the medium discharging the heating device,
    controlling the heating device by setting a temperature in the heating device so that the medium discharging from the heating device is of a prescribed temperature,
    said setting of a temperature in the heating device is performed by measuring the temperature in a place between said heating element and the flowing medium, producing a first signal proportional to the temperature measured in said place, producing a second signal on the basis of the temperatures of the entering and discharging medium, as well as of the specific heat, the flow rate and the prescribed temperature of the medium, and controlling said heating element according to the difference between said first and second signals.

17. A method for controlling the temperature of a flowing medium comprising the steps of:
    causing the medium to flow through a heating device having a heating element,
    measuring the temperature of the medium entering the heating device,
    measuring the temperature of the medium discharging the heating device,
    controlling the heating device by setting a heat flux in the heating device so that the medium discharging from the heating device is of a prescribed temperature,
    said setting of a heat flux in the heating device is performed by measuring the temperatures in two places behind each other in the direction of the heat flux between said heating element and the flowing medium, producing a first signal proportional to the difference of the measured temperatures in said two places, producing a second signal in the basis of the temperatures of the entering and discharging medium, as well as of the specific heat, the flow rate and the prescribed temperature of the medium, and controlling said heating element according to the difference between said first and second signals.

18. The method according to claim 16, or claim 17, wherein the flow rate of the entering medium is measured before the measurement of the temperature of the entering medium, and said second signal is produced by taking into account said measured flow rate.

* * * * *